United States Patent [19]

Strandberg, Jr. et al.

[11] Patent Number: 4,525,937

[45] Date of Patent: Jul. 2, 1985

[54] MOISTURE MONITORING DRYER CONTROL APPARATUS

[75] Inventors: Charles F. Strandberg, Jr., High Point; Robert C. Strandberg, Greensboro, both of N.C.

[73] Assignee: Strandberg Engineering Laboratories, Inc., Greensboro, N.C.

[21] Appl. No.: 604,980

[22] Filed: Apr. 27, 1984

[51] Int. Cl.³ ............................................. F26B 21/10
[52] U.S. Cl. .......................................... 34/48; 34/50; 34/53; 34/55
[58] Field of Search .................... 34/48, 50, 53, 55; 324/65 R, 65 P

[56] References Cited

U.S. PATENT DOCUMENTS

| 2,047,638 | 7/1936 | Kott | 73/336.5 |
| 2,859,318 | 11/1958 | Ohlheiser | 338/35 |
| 3,073,161 | 1/1963 | Crabtree | 73/336.5 |
| 3,110,005 | 11/1963 | Kripke | 338/35 |
| 3,167,734 | 1/1965 | Brucken et al. | 338/35 |
| 3,170,774 | 2/1965 | Deaton | 34/45 |
| 3,315,518 | 4/1967 | Charlson et al. | 73/29 |
| 4,270,085 | 5/1981 | Terada et al. | 324/65 R |
| 4,388,766 | 6/1983 | Sanderson | 34/54 |

Primary Examiner—Larry I. Schwartz
Assistant Examiner—David W. Westphal
Attorney, Agent, or Firm—Munson H. Lane, Jr.

[57] ABSTRACT

A moisture monitoring dryer control apparatus for a dryer having an electrically operated motor, a heater and an exhaust duct through which air from the dryer passes whose humidity level signifies the residual moisture in the goods being dried. The apparatus comprises a moisture sensor assembly to be installed in the dryer air exhaust duct, and a dryer control and display unit electrically connected to the sensor to receive electrical signals therefrom. The moisture sensor being a resistance type includes a head portion housing a thin piece of hygroscopic material sandwiched between a front porous filter member and a perforated backing plate in substantially coextensive relation, a pair of electrical conductors connected respectively to the filter member and the backing plate and to electrical circuitry in the control and display unit, a high resistance air sample cup member engaging and extending rearwardly from the filter member forming a substantially closed chamber rearwardly of the perforated plate into which air can enter through the porous filter but must return therethrough, and an elongated extension tube member having the head portion of the sensor carried on an end thereof to be supported by the tube member in an air sensing position in the exhaust duct with the longitudinal axis of the tube member arranged perpendicular to the direction of air flow through the duct and perpendicular to the sandwiched hygroscopic material piece, backing plate and filter member.

14 Claims, 6 Drawing Figures

AIR FLOW DIRECTION

4,525,937

MOISTURE MONITORING DRYER CONTROL APPARATUS

BACKGROUND AND OBJECTS OF THE INVENTION

The present invention relates, in general, to moisture monitoring dryer control apparatus, and, more particularly, to moisture control apparatus for use with many standard forms of commercial, institutional, industrial and domestic tumbler dryers for terminating the drying cycle when the residual moisture in the goods being dried reaches a desired level and initiating a cool-down cycle to deliver the goods at near room temperature conditions.

Heretofore, various types of dryer control apparatus have been developed, involving some kind of moisture sensing device which undergoes change in its electrical properties in some relationship to moisture present in the air being monitored, to determine when clothes being dried in a tumbler dryer have reached a predetermined state of dryness, providing electrical or electronic circuitry to turn off the dryer heater when the pre-determined dryer condition has been reached and allow the dryer to continue operating to cool the clothes before stopping the ventilating and tumbling operation. Some of such devices rely upon change in leakage of voltage across the sensor device at a rate dependent on the moisture content of the clothes, and some involve changes in electrical resistance path bearing a relationship to the moisture.

The present invention is designed to provide moisture monitoring apparatus for commercial, institutional, industrial and domestic tumbler dryers and the like having an improved humidity sensor of rugged and reliable construction capable of sustained operation in high-temperature dryers without degradation in overall system performance, wherein control circuitry is provided for terminating the drying cycle when the residual moisture of the goods being dried reaches the desired level and initiate cool-down cycle to deliver the goods at near room temperature, and which includes adjustment means for conveniently presetting the desired degree of dryness to be attained.

Another object of the present invention is to provide moisture monitoring and dryer control apparatus having visual display means in an LED bargraph display, to enable the operator to observe the progress of the drying cycle and optimize dryer loads.

A still-further object of the present invention is to provide a moisture monitoring and dryer control apparatus as described in the preceding paragraph, including sensing means for verification of dryer run status and control means for automatic termination of the drying cycle and initiation of the cool-down cycle.

Other objects, advantages and capabilities will become apparent from the following detailed description, taken in conjunction with the accompanying drawings illustrating a preferred embodiment of the invention.

DETAILED DESCRIPTION OF A PREFERRED EMBODIMENT

Figure 1:
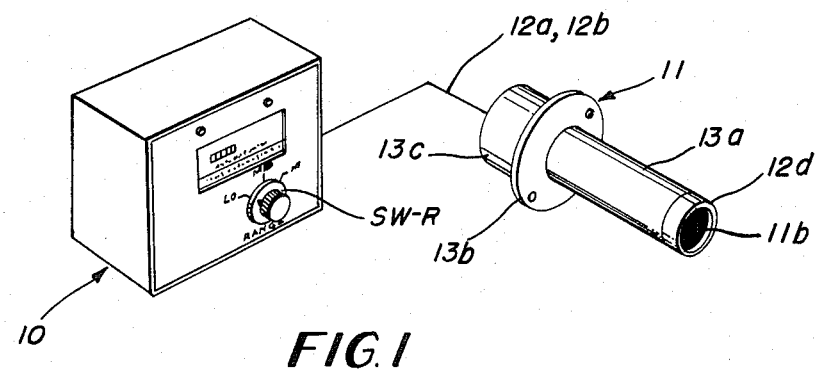
FIG. 1 is a perspective view of the main control and display unit and the moisture sensor assembly of the moisture monitoring dryer control apparatus of the present invention.

Referring to the drawings, wherein like reference characters designate corresponding parts throughout the several figures, the moisture monitoring dryer control apparatus of the present invention comprises a main control and display unit, shown in the illustrated embodiment as a generally box-like console or component 10, which is interconnected by wiring to a moisture sensor assembly, indicated at 11, designed to be placed in a dryer exhaust duct to sense the exhaust humidity and provide related electrical voltages to the control and display unit 10. In broad terms, the humidity sensor 11 is connected in series with a variable resistor in the circuitry of the main control unit 10, and with a DC voltage source. The humidity or moisture sensor 11 include a thin piece of hygroscopic material to each side of which electrical connection is made. The electrical resistivity of this material varies inversely with the humidity level of the air surrounding the sensor. Therefore, with the value of the variable resistor set at some value approximating that of the sensor material at standard conditions, the voltage drop across the resistor is directly proportional to the humidity level, and, with equal resistance, displays maximum sensitivity to variations in humidity, since the response characteristic or curve has a constant slope and is linear along the operating region of the apparatus.

Figure 3:
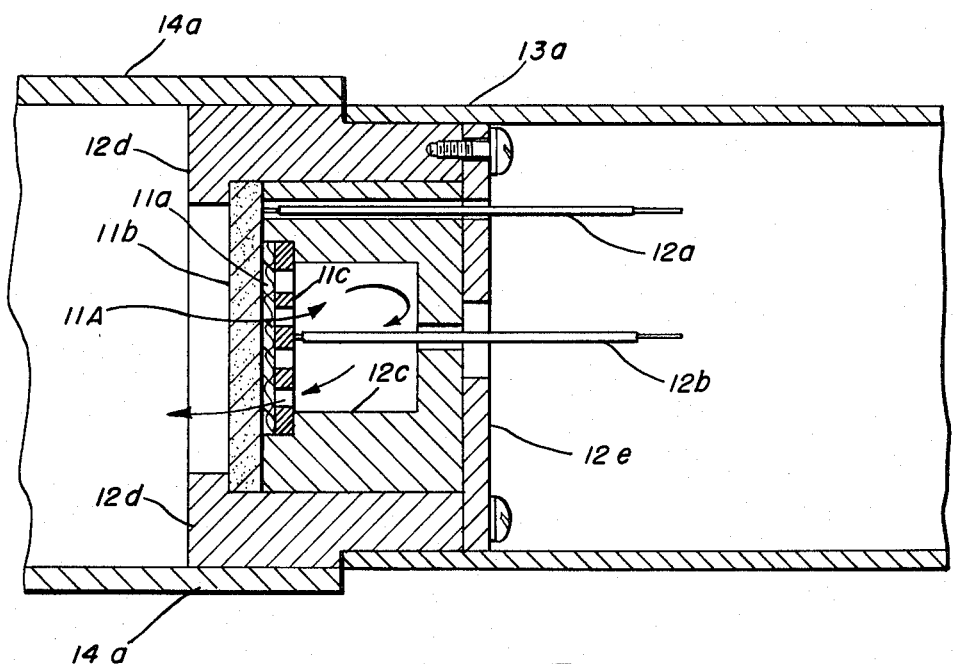
FIG. 3 is a vertical section view through the sensor and adjacent parts of the extension tube.

In the preferred embodiment, the sensor 11 includes a piece of hygroscopic material, indicated at 11a in FIG. 3, preferably cotton cloth, sandwiched between a porous filter 11b, normally of sintered steel, and a perforated stainless steel plate 11c to which electrical conductors 12a and 12b are connected. The cotton cloth 11a is preconditioned to stabilize its electrical resistance characteristics against drift by heating it to a suitable high temperature of about 250° F. for a substantial period of time, of about 12 hours or longer. A high resistance air sample cup 12c positioned behind the perforated plate 11c hold the perforated plate firmly against the piece of material 11a, to ensure good electrical contact, and provides a chamber into which air can enter, but, because the bottom of the cup is essentially closed except for the passage through which the conductor 12b extends, the air entering the chamber through the porous filter 11b must also exit through the porous filter. Since air is not continuously passing through the filter 11b in one direction, the tendency for lint and other trash material in the air duct in which the sensor is mounted to accumulate on the face of the filter 11b is substantially reduced and air exiting from the cup 12c through the filter 11b provides a cleansing action.

Figure 2:
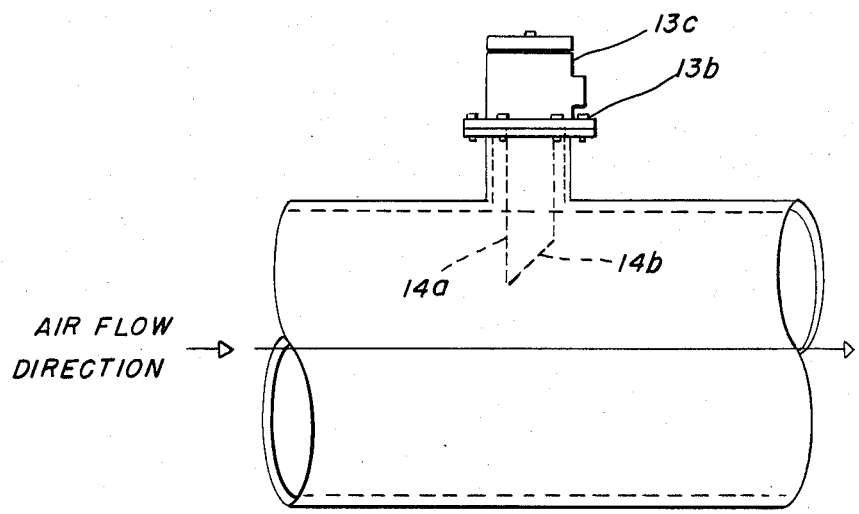
FIG. 2 is a fragmentary elevation view of the moisture sensor shown mounted in position in a dryer exhaust duct.

Each of the previously described parts of the sensor are mounted in the housing end cap 12d, and retained securely by the retainer plate 12e. An extension tube 13a fixed at one end to the housing end cap 12d has a suitable mounting flange plate or formation 13b for securing the extension tube 13a and sensor head components to a conduit outlet body member 13c. The sensor unit is normally mounted in the exhaust duct of a tumbler dryer with its longitudinal axis perpendicular to the axis of the exhaust duct and to the direction of air flow. As shown in FIG. 2, a typical installation, a shroud 14a, also shown in part and FIG. 3, is attached over the housing end cap 12d of the sensor unit to provide further protection for the sensor from debris in the exhaust air. The end of this shroud 14a is cut at about 45° angle to its axis, as indicated at 14b, and the shroud is oriented so that its angled face faces downstream.

The sensor input terminals 12a', 12b' are connected via input wires 12a and 12b to the main control and display unit 10. A dryness range selection switch SW-R is connected to the sensor, as shown schematically in FIG. 4, and allows selection of one of several fixed resistors R1, R2, or R3. These resistors correspond to the variable resistor referred to in the previous generalized discussion, and serve to select the desired degree of dryness. A control knob for the movable arm of the dryness range selection switch is accessible on the front of the main control unit 10, also indicated there by the reference character SW-R. Three resistors are illustrated in the described embodiment, but more can be employed to yield a finer degree of dryness selection if desired. The voltage drop across the selected resistor is sensed by a high-input impedance voltage follower 16, and converted to a low impedance signal to drive subsequent circuitry. A standard bargraph LED voltmeter display 17 or alternate mechanical meter provides a visual indication of the moisture in the goods being dried.

Figure 4:
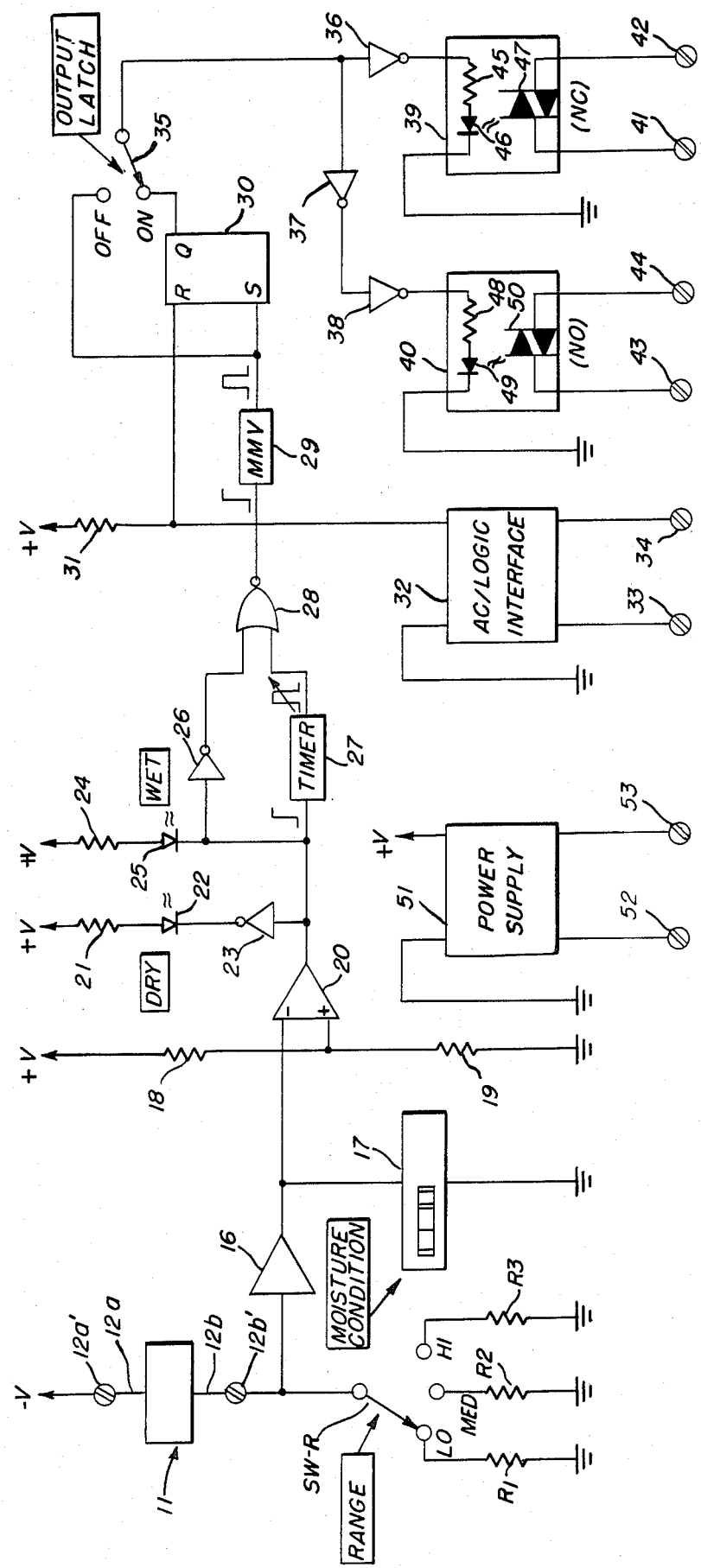
FIG. 4 is a simplified electrical schematic diagram of the moisture monitor.
Figure 5:
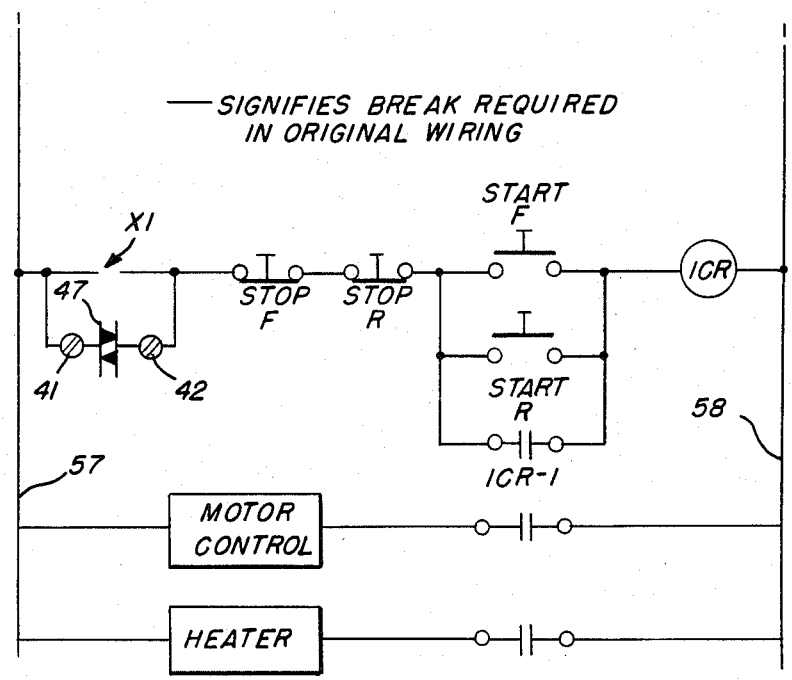
FIGS. 5 and 6 are electrical diagrams showing interconnections with typical dryer-control wiring.
Figure 6:
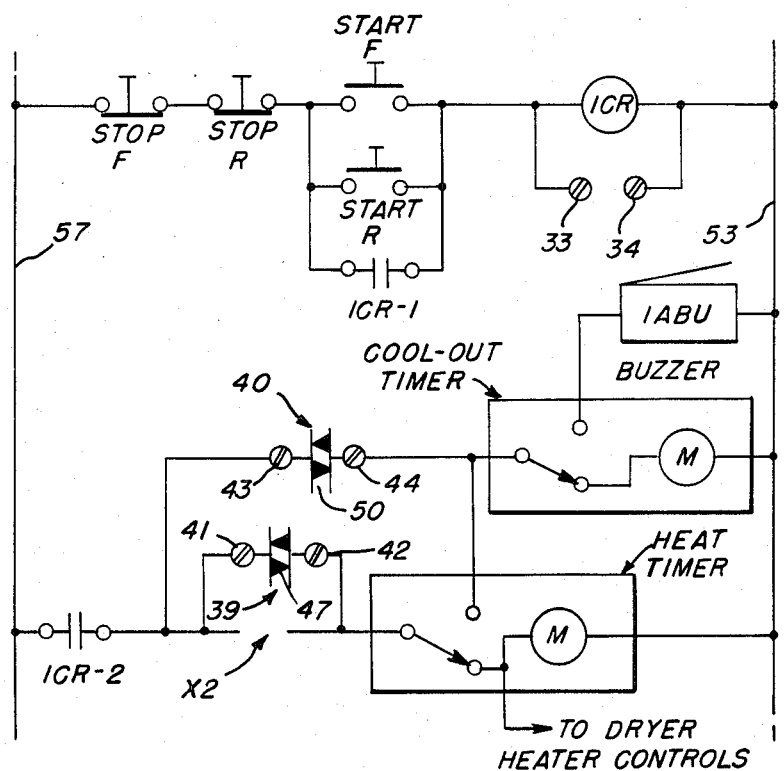

Prior to describing the operation of the circuit shown in FIGS. 4, 5 and 6 in detail, a brief discussion of the power supply, shown at 51, and the AC/logic interface 32, and the operation of the latter may assist understanding of the subsequent detailed description. The power supply 51, shown in FIG. 4, connected to power input terminals 52 and 53, is a conventional power supply with step-down transformer, rectifier, and regulator. The regulated output voltage +V is typical +5 volts. The AC/logic interface 32, as shown, is a Hewlett Packard HCPL-3700 which is used to sense the dryer run relay coil voltage to determine if the dryer is running or stopped. This device is a preferred interface device for logic circuitry but other devices such as spare run relay contacts can be alternately employed. Operation of the interface circuit is essentially as follows: when an AC voltage is sensed at run status terminals 33 and 34, the output of the interface 32 connected to resistor 31 is pulled to ground. When the AC voltage is interrupted, the output of the interface, is pulled up to +V through resistor 31. The solid-state relays 39 and 40 are conventional solid-state relays which are preferred for improved reliability, for example, International Rectifier Crydom D2410 or equivalent. Electromechanical relays may be alternately used, however, if desired.

There are two basic dryer interface configurations that are normally encountered. The first is where it is desired to simply stop the dryer in much the same way as depressing a stop pushbutton switch momentarily. This interface is illustrated in FIG. 5. The wiring is broken at point Xl as shown in FIG. 5 as well as FIG. 4. and the connections are made to the normally closed relay 39, terminals 41 and 42, thereby placing the solid-state relay out-put device 47 in series with the control relay 1CR and stop and start pushbutton switches between the control voltage lines 57 and 58. The output latch switch 35 must be set to OFF for this application. Note that no connection is required to the AC/logic interface 32, terminals 33 and 34.

Operation of the device is as follows: with the dryer stopped, the humidity at the humidity sensor 11 is low. Therefore, the voltage at the output of voltage follower 16 is low and the moisture condition display 17 indicates at the dry end. Resistors 18 and 19 form a voltage divider to obtain a reference voltage for comparator 20. A suitable reference voltage is obtained by making the value of resistor 18 the same as the value of resistor 19. This gives a reference voltage at the positive input to comparator 20 equal to one half of +V. With the voltage at the negative input of comparator 20 less than +V/2, the output of comparator 20 is high. The output of inverter 23 is low and the Dry LED 22 is energized. Resistor 21 serves to limit the current through the LED 22.

While the output of comparator 20 is high and the Dry LED 22 is energized, the output of NOR gate 28 is high and the output of monostable multivibrator 29 is low. The MMV 29 may be a Signetics NE555 with a standard inverter in the input. With the output latch switch 35 positioned to OFF, the inputs to inverters 36 and 37 are also low. Therefore, the output of invertor 36 is high and it therefore supplies current through resistor 45, to the LED 46 in the solid state relay 39. The solid-state relay output device 47 is thereby energized allowing the dryer to be started by depressing either start pushbutton switch.

When the dryer is started, the exhaust humidity level increases as heated air is blown through the wet goods. This results in a corresponding drop in the resistivity of the humidity sensor 11 thereby causing an increase in the voltage drop across the selected range resistor R1, R2 or R3 and an increase in the voltage output from the follower 16. As this voltage exceeds +V/2, the output of comparator 20 abruptly drops to ground potential. The Dry LED 22 turns off with the output of inverter 23 now high, and the Wet LED 25 is energized, signifying that the moisture condition in the goods is now above the preset cut-off level.

As the output of comparator 20 goes low, the output of inverter 26 goes high causing the output of NOR gate 28 to go low. This causes no change in the output of MMV 29 since this device is only triggered by a positive-going input transition.

The timer 27 is also a positive edge triggered device and so is not affected by the low going output form comparator 20. The timer 27 may be a Signetics NE555 with a standard inverter in the input, and have typical time range from about 0.5 second to 30 seconds.

As the moisture in the goods in the dryer slowly decreases toward the desired cut-off level, the output of the voltage follower 16 decreases and finally drops below +V/2 at which point the output of comparator 20 goes high. The Dry LED 22 is energized and the Wet LED 25 turns off. Also, the output of timer 27 goes high and the output of inverter 26 goes low. The input-to-output delay time or propagation delay of inverter 26 must exceed the propagation delay of the timer 27. This insures that the output of the NOR gate 28 remains low until the timer output returns to a low level. After the timer output delay time expires and both inputs to NOR gate 28 are low, the MMV 29 is triggered by the positive going output from the NOR gate 28. A positive pulse of from one to two seconds duration is thereby delivered to the inverter 36 causing the normally closed relay 39 to momentarily open. This action caused the dryer to stop in the same manner as depressing either of the stop pushbutton switches.

The combination of the inverter 26, timer 27, and NOR gate 28 comprises a retriggerable stop delay and is included to interface with modulating dryer heaters. In some dryers the heaters are modulated on and off to apparently reduce the risk of scorching the goods which also reduces the risk of fires. This modulation in the heaters results in an attendant modulation in the sensed exhaust humidity as the level decreases to see this effect on the moisture condition display 17 and Dry and Wet LEDS and so the stop delay circuitry was added to prevent the dryer from being stopped prematurely. The delay time is adjustable to compensate both for various heater modification rates and inherent dryer delay characteristics.

The second dryer interface configuration that is normally encountered requires interconnecting with existing heat and cool-out timers. Here it is desired to bypass the existing heat timer and automatically energize the existing cool-out timer. This interface is illustrated in FIG. 6. Since the relay outputs must by-pass existing timer controlled contacts, the relay output status must be maintained. Therefore, the output latch switch 35 must be set to ON for this application. Also, to reset the latch, the AC/logic interface 32 must be connected across the dryer run relay coil.

As in the first dryer interface configuration, the original wiring is broken as shown at X2 and connections are made to the relay terminals 41, 42, 43 and 44 and to the AC/logic interface terminals 33 and 34. The heat timer is still in circuit and will both deactivate the heater controls and initiate the cool down cycle if the set time expires prior to the dryer being stopped automatically by the moisture control.

Operation of the device is as follows: circuit conditions for this interface configuration are essentially as before except now the AC/logic interface 32 is active. With the dryer stopped, the output of the AC/logic interface 32 is pulled high by resistor 31. The output of the AC/logic interface went high when the dryer was last stopped. This high on the R (Reset) input of the RS flip-flop 30 reset the Q output low which, via the output latch switch 35 and inverters 36, 37 and 38, reset the solid state relay 39 to the on or conducting state for the normally closed condition and reset solid state relay 40 to the off or non-conducting state for the normally open condition. The reset flip-flop 30 may be a standard RS flip-flop made up of two 2-input positive NOR gates such as Texas Instruments SN7402.

As before, with the dryer stopped, the humidity at the sensor is low resulting in a high output form the comparator 20. The Dry LED 22 is energized, and the outputs of inverter 26 and timer 27 are low causing the output of NOR gate 28 to be high. The output of the MMV 29 is low.

When the dryer is started the output of comparator 20 eventually goes low as the exhaust humidity rises. After the residual moisture level in the goods slowly decreases to the desired cut-off level, the output of comparator 20 once again goes high causing the Dry LED 22 to be energized and triggering the timer 27. After the timer output delay time expires the output of NOR gate 28 goes high thereby triggering MMV 29. The momentary high output from MMV 29 sets the RS flip-flop Q output high. This latches solid state relay 39 to the off or non-conducting state and solid state relay 40 to the on or conducting state causing the heat timer and dryer timer to be energized. After the cool-out timer runs out, a buzzer is activated to alert operators that the dryer should be stopped and unloaded. When the operator stops the dryer by depressing one of the stop pushbutton switches, the AC voltage across the run relay coil 1 CR drops to zero thereby triggering the AC/logic interface. The output of the AC/logic interface goes high resetting the RS flip-flop 30 and restoring the normal status of both solid state relays. The dryer heat and cool-out timers are now reenabled preparatory to the next dryer start-up.

While a preferred embodiment of circuitry for the present invention has been specifically shown and described, it will be apparent that changes in circuitry could be made without departing from the scope of the invention. It is therefore intended that the example herein described be considered as illustrative and not construed as limiting.

What is claimed:

1. A moisture monitoring dryer control apparatus for a dryer of goods having electrically operated motor means and heater means and an exhaust duct through which air from the dryer passes whose humidity level signifies the residual moisture in the goods being dried, the apparatus comprising a moisture sensor assembly to be installed in the dryer air exhaust duct for sensing the humidity of the air exhausting therethrough and a dryer control and display unit electrically connected to the sensor to receive electrical signals therefrom, the moisture sensor being a resistance type includes a head portion housing a thin piece of hygroscopic material of predetermined small area having front and back faces and sandwiched between a front porous filter member and a perforated backing plate in substantially coextensive relation in close physical contact with the front and back faces of said piece of hygroscopic material over the whole area thereof, a pair of electrical conductors connected respectively to said filter member and said backing plate and to electrical circuitry in said control and display unit, a high resistance air sample cup member engaging and extending rearwardly from said filter member forming a substantially closed chamber rearwardly of said perforated plate into which air can enter through the porous filter but must return therethrough, an elongated extension tube member having said head portion of the sensor carried on an end thereof to be supported by the tube member in an air sensing position in said exhaust duct with the longitudinal axis of the tube member arranged perpendicular to the direction of air flow through the duct and perpendicular to the sandwiched hygroscopic material piece, backing plate and filter member.

2. Apparatus as defined in claim 1, wherein said head portion of said sensor is an annular end cap member encircling said cup member and the sandwiched hygroscopic material piece, backing plate and filter member positioned thereagainst forming a substantially cylindrical sensor head with the filter member exposed at one end thereof for exposure to the air in said exhaust duct.

3. Apparatus as defined in claim 2, including a tubular elongated shroud member extending from and joint at one end to said head portion in coaxial relation to the axis of said extension tube to project a predetermined distance beyond the filter member into air flow in the exhaust duct and having the end of the shroud opposite said one end cut at an acute angle of about 45° to said axis and oriented to dispose the angled end in a downstream facing direction within the duct to afford protection for the sensor from debris in the air flowing through the exhaust duct.

4. Apparatus as defined in claim 3, wherein said porous filter member is a plate-like body of sintered steel and said backing plate is a perforated stainless steel plate.

5. Apparatus as defined in claim 2 wherein the piece of hygroscopic material is cotton cloth having its electrical resistance characteristics stabilized against drift by heating to a temperature of about 250° F. for a time period of at least about 12 hours.

6. Apparatus as defined in claim 5, wherein said porous filter member is a plate-like body of sintered steel and said backing plate is a perforated stainless steel plate.

7. Apparatus as defined in claim 2, wherein said porous filter member is a plate-like body of sintered steel and said backing plate is a perforated stainless steel plate.

8. Apparatus as defined in claim 1, including a tubular elongated shroud member extending from and joint at one end to said head portion in coaxial relation to the axis of said extension tube to project a predetermined distance beyond the filter member into air flow in the exhaust duct and having the end of the shroud opposite said one end cut at an acute angle to said axis and oriented to dispose the angled end in a downstream facing direction within the duct to afford protection for the sensor from debris in the air flowing through the exhaust duct.

9. Apparatus as defined in claim 8 wherein the piece of hygroscopic material is cotton cloth having its electrical resistance characteristics stabilized against drift by heating to a temperature of about 250° F. for a time period of at least about 12 hours.

10. Apparatus as defined in claim 9, wherein said porous filter member is a plate-like body of sintered steel and said backing plate is a perforated stainless steel plate.

11. Apparatus as defined in claim 8, wherein said porous filter member is a plate-like body of sintered steel and said backing plate is a perforated stainless steel plate.

12. Apparatus as defined in claim 1 wherein the piece of hygroscopic material is cotton cloth having its electrical resistance characteristics stabilized against drift by heating to a temperature of about 250° F. for a time period of at least about 12 hours.

13. Apparatus as defined in claim 12, wherein said porous filter member is a plate-like body of sintered steel and said backing plate is a perforated stainless steel plate.

14. Apparatus as defined in claim 1, wherein said porous filter member is a plate-like body of sintered steel and said backing plate is a perforated stainless steel plate.

* * * * *